United States Patent [19]

Buchholtz et al.

[11] Patent Number: 4,808,089
[45] Date of Patent: Feb. 28, 1989

[54] RECIPROCATING PUMP FOR A MEDICATION ADMINISTERING DEVICE

[75] Inventors: Gerhard Buchholtz; Werner Fickweiler; Peter Obermann, all of Erlangen, Fed. Rep. of Germany

[73] Assignee: Siemens Aktiengesellschaft, Berlin and Munich, Fed. Rep. of Germany

[21] Appl. No.: 91,721

[22] Filed: Sep. 1, 1987

[30] Foreign Application Priority Data

Sep. 1, 1986 [DE] Fed. Rep. of Germany ....... 3629698

[51] Int. Cl.$^4$ .............................................. F04B 17/04
[52] U.S. Cl. .................................. 417/417; 417/505; 417/570; 604/152
[58] Field of Search ............... 417/505, 417, 570; 604/151, 152; 251/364, 333

[56] References Cited

U.S. PATENT DOCUMENTS

| | | | |
|---|---|---|---|
| 2,693,767 | 11/1954 | Vroman | 417/505 |
| 3,302,582 | 2/1967 | Kofink | 417/417 |
| 3,544,065 | 12/1970 | Merceir | 251/333 X |
| 3,974,854 | 8/1976 | Kurpánek | 137/512 |
| 4,437,815 | 3/1984 | McMullen | 417/505 X |
| 4,482,346 | 11/1984 | Reinicke | 604/152 |
| 4,531,895 | 7/1985 | Zeck | 417/570 X |

FOREIGN PATENT DOCUMENTS

| | | |
|---|---|---|
| 0102824 | 3/1984 | European Pat. Off. . |
| 0103536 | 3/1984 | European Pat. Off. . |
| 0110117 | 6/1984 | European Pat. Off. . |
| 1911649 | 9/1970 | Fed. Rep. of Germany . |

Primary Examiner—Leonard E. Smith

[57] ABSTRACT

A reciprocating pump having a fluid assembly having a fluid wing at its input side encompassing an admission line and an admission chamber. A moveable valve part of, for example, a magnetizable material is arranged in the admission chamber. A component part, for example a permanent magnet, which attracts the valve part against a valve seal is situated outside of the fluid wing. The valve part and the component part together form a magnetic spring system. An advantage of this arrangement is an extremely small dead spacing inside the fluid wing. Resulting therefrom is that gas bubbles can also be conveyed with great reliability. Also harmful interaction between the conveyed medication and the component part such as, for example, corrosion of the component part or conversions of the medication influenced by the component part, cannot occur.

2 Claims, 1 Drawing Sheet

U.S. Patent    Feb. 28, 1989    4,808,089
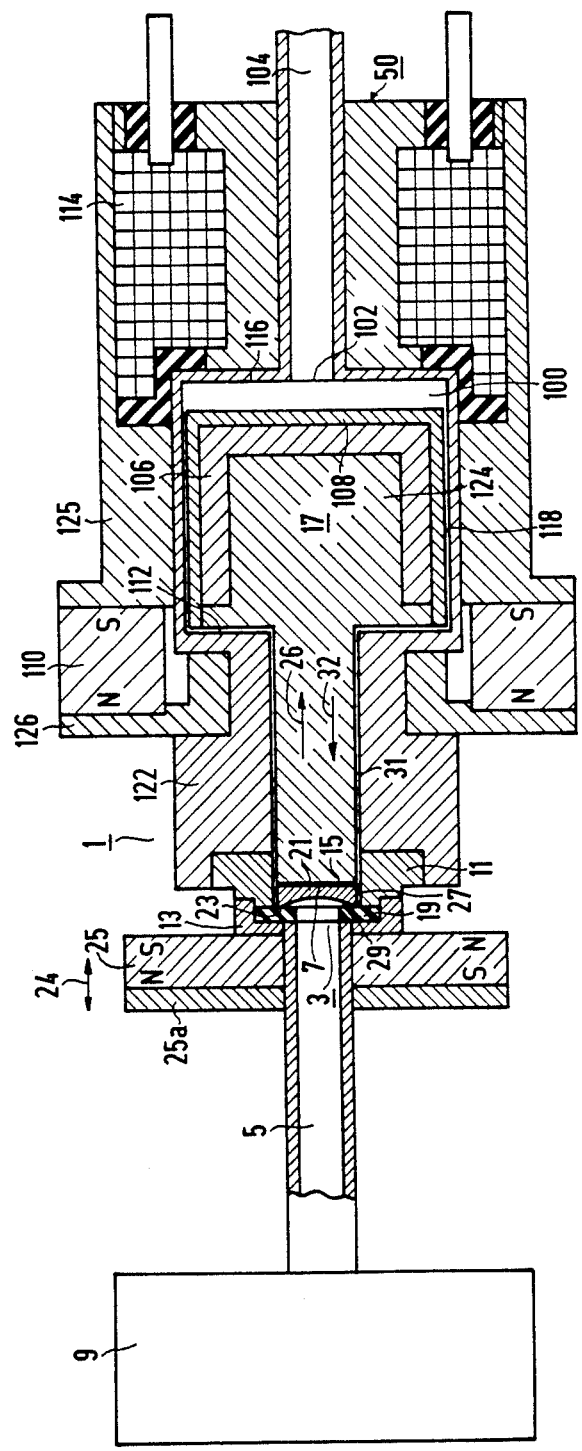

RECIPROCATING PUMP FOR A MEDICATION ADMINISTERING DEVICE

BACKGROUND OF THE INVENTION

The invention is directed to a reciprocating pump for a use as a medication administering device and has a piston which is displaceable with an actuation means. An admission fluid wing encompasses an admission line and an admission chamber, and has a valve part moveable in the admission chamber which is provided for closing an admission opening at the admission line.

For reasons of miniaturization, it is advantageous to utilize a miniaturized reciprocating pump as a pump unit in an implantable medication administering device. The piston displacement of such a pump needed in this application lies on the order of magnitude of 1 $\mu$l. The pump should also be capable of pumping gas bubbles with a satisfactory conveying rate so that, given the appearance of a gas bubble in the fluid wing, the patient need not do without the medication. For example, a gas bubble in the medication reservoir arises due to the degasification of the medication or when replenishing medications. The problem of gas bubble conveying is raised to an even greater degree in medication dosing devices wherein the medication reservoir is charged with a low pressure. Such a low pressure in the medication reservoir is advantageous for safety-related reasons and typically fluctuates between 0.5 and 1 bar absolute. Given an ideal pump having an admission chamber free of dead space, a reduction of the gas conveying rate at the lower limit of the low pressure (0.5 bar absolute) thereby derives by the factor two in comparison to the fluid conveying rate for physical reasons. When a pump has a dead space in an admission chamber having the same size as the piston displacement, then physical reasons make a conveying of gas bubbles impossible at the lower limit of the low pressure (0.5 bar absolute) in the reservoir system. A gas bubble situated in the admission chamber is merely compressed and decompressed without having a conveying event toward the exit side occuring.

It is desirable for these reasons to have the greatest possible ratio of piston displacement to dead space in the admission chamber in a reciprocating pump. Since small quantities of fluid are to be conveyed in a medication administering device, an enlargement of the piston displacement of the reciprocating pump is usually not possible. The point of attack for achieving a high gas conveying rate thus lies in reducing the dead space.

A reciprocating pump of the species initially cited is disclosed by U.S. Pat. No. 3,568,250, particularly FIGS. 2 and 3. This provides an admission chamber which is formed by the end face of the piston, by a cylindrical wall and by an end face of a housing having an opening for an admission line. A moveable valve part is arranged inside the admission chamber. A coil spring holds the valve part pressed against the admission opening in a quiescent condition. A relatively large dead space arises due to the coil spring with the appertaining fastening means, this dead space potentially having an unfavorable effect on the gas conveying rate of the reciprocating pump.

German published application No. 19 11 649, FIGS. 1 through 4, shows an over-flow valve which is preferably utilized as a safety and control valve in blood circulations. The valve has a valve part having a magnetic closing force which can be adjusted from the outside. Here, however, the valve part and the valve seat are fashioned in a flow-beneficial way. That means that no sharp transmissions or salient mounts are present, this leading to considerable dead space. Further, a leak flow is present according to FIGS. 2 and 4 given a closed valve in order to prevent the formation of trickling. This design also means the presences of considerable dead spaces.

SUMMARY OF THE INVENTION

An object of the invention is to provide a reciprocating pump of the species initially cited which has a small dead space at its input side and thus enables a high gas conveying rate.

This object is inventively achieved in that the valve part is accomodated in freely mobile fashion in the admission chamber; in that the end faces of the piston forms one wall of the admission chamber; in that a gap is provided between the piston and the surrounding cylinder wall; and in that a component part is in magnetic interaction with the valve part and forms a magnetic spring system therewith which is arranged outside of the admission fluid wing. This spring system exerts a closing force on the valve part for closing the admission opening.

An especially advantageous embodiment of the reciprocating pump is characterized in that the valve part is partially or completely composed of a magnetizable material and the component part is a permanent magnet.

In the one component part (permanent magnet or element of magnetic material) of the spring system which is not situated in the admission chamber but which is outside of the admission fluid wing, the ratio of piston displacement to dead space of the admission chamber is high, a high gas conveying rate being possible on the basis thereof.

Deriving as a further advantage is that the force acting on the valve part due to the magnetic effect penetrating the pump chamber walls can also be subsequently adjusted from the outside, i.e. after the reciprocating pump has already been assembled. The reliability is guaranteed by the employment of the magnetic spring system. The material fatigue and/or corrosion involved with a mechanical spring does not occur. Further, it is possible to design the valve part situated in the admission chamber simply and planarly, this having a beneficial effect when pumping medications having a tendency to sediment such as, for example, insulin. Also eliminated by arranging the component part outside of the admission chamber are problems which could arise due to an interaction of the medication with the material of a mechanical spring arranged at the inside. First, no attention need be given to be medication compatability of the spring material and, second, there is no risk of a toxicity of the medication produced by the spring material, for example due to releasable nickel constituents in the spring material.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several figures of which like reference numberals identify like elements, and in which:

The single FIGURE shows a schematic cross-sectional view of the reciprocating pump for the medication dosing having a magnetic spring system at the admission chamber.

DESCRIPTION OF THE PREFERRED EMBODIMENT

According to the FIGURE, the input side of a reciprocating pump 1 has a fluid wing or section 3 between an admission line 5 and an admission chamber 7. One side of the admission line 5 is connected to a medication reservoir 9 which is preferably charged with a low pressure. The other side of the admission line 5 discharges into the admission chamber 7.

The admission chamber 7 is limited by a cylindrical jacket part 11, by an end face 15 of a piston 17 and by the generated cylindrical surface, as well, as by the planar surface of a valve part 21. A flange 13 connects to the jacket part 11 and has a central opening at whose edge the admission line 5 is secured by gluing or welding. Alternatively thereto, it is possible to manufacture the flange 13 and the admission line 5 as one part. In the preferred embodiment the jacket part 11 has an inside diameter of about 2 mm.

A ring-shaped valve seal 19 presses against the flange 13, this valve seal 19 being pressed against the flange 13 by the cylindrical jacket part 11. The valve seal 19 has a central opening which corresponds to the inside cross-section of the admission line 5. The moveable valve part 21 is arranged inside the admission chamber 7 and is shaped such that it forms a liquid-tight and gas-tight closure when seated against the valve seal 19. In the preferred embodiment, the valve part 21 is hollowed out such that at its sealing side, it is inwardly arced with a cutting edge 23 present at the edge which is pressed resiliently against the valve seal 19 in the quiescent condition of the reciprocating pump. At its other side, the valve part 21 has a planar end face.

The sealing valve seat of the valve part 21 in the quiescent condition, i.e. its seating against the valve seal 19, is achieved by a component part 25, which is a permanent magnetic system in the preferred embodiment Here, this component part 25 is composed, for example, of two cube or block-shaped permanent magnets which are secured, lying opposite one another, on a magnetic return 25a composed of a magnetizable material. The north and south poles are referenced N and S respectively. It is seated firmly on the admission line 5 and forms a magnetic spring system together with the valve part 21. It thereby draws the valve part 21 composed of magnetizable material against the valve seal 19 on the basis of a magnetic field effect. It is likewise possible to manufacture the valve part 21 from a permanent magnet. In this case, it is possible to design the component part 25 as a permanent magnet or as a component part composed of the magnetizable material. Alternatively, the component part 25 in the form of a permanent magnet can also be arranged at the other side, i.e. at the right side, of the valve seat 21 and can generate a pressing force against the valve seal 19 instead of generating an attracting force. What is thereby critical is that the component part 25 (i.e., the permanent magnet or, as an alternative, the magnetizable material) is arranged outside of the fluid wing 3. In this way, no unnecessary dead space arises within the fluid wing 3, particularly inside the admission chamber 7.

The component part 25 is expediently displacable arranged along the symmetrical axis or longitudinal axis of the valve part 21. This is indicated by a double arrow 24. This enables the restoring force on the valve part 21 to be subsequently adjusted given a completely assembled pump 1.

During operation of the reciprocating pump 1, the piston 17 is moved toward the right in the direction of the arrow 26, being moved, for example, by electromagnetic field action as shall be set forth later, whereby a strong low pressure is created in the admission chamber 7. As soon as the force exerted on the moveable valve part 21 due to the low pressure in the admission chamber 7 exceeds the restoring force of the magnetic spring system, the cutting edge 23 of the moveable valve part 21 lifts off from the valve seat 19 and a valve gap 29 is opened between the moveable valve part 21 and the valve seal 19. Due to the great low pressure in the admission chamber 7, the medication is suctioned thereinto from the low pressure in the medication reservoir 9. It thereby flows through the admission line 5, through the opened valve gap 29 between the moveable valve part 21 and the valve seal 19 and through a gap 27 between the edge of the moveable valve part 21 and the cylindrical jacket part 11. When the piston 17 has reached its lift position, the great low pressure in the admission chamber 7 is reduced due to the inflowing medication. As soon as the force exerted on the moveable valve part 21 by the low pressure in the admission chamber 7 falls below the restoring force of the spring system, the valve part 21 is again completely lowered onto the valve seal 19 and the valve gap 29 is closed.

Liquid medication is now situated between the end face 15 of the piston 17 and the planar end face of the valve part 21. When the piston 17 is moved from its lift position into its (illustrated) lower position in the direction of the arrow 32, then a pressure is exerted on the medication situated in the admission chamber 7. As a result thereof, the medication is pressed through an annular gap 31 between the piston 17 and the guide housing 122 thereof, being pressed in the direction toward a discharge line 104 at the discharge system 50. The gap 31 can also be fashioned in the form of one or more longitudinal channels.

As already mentioned, the piston 17 is likewise guided by a magnetic spring system 106, 110 and is shown in its quiescent position, i.e. in its lowering position in the FIGURE. The means required for this purpose are set forth below.

The discharge system 50 has a pump chamber 100 which has a discharge opening 102. A discharge line 104 leads from the discharge opening 102 to a catheter connection (not shown). The pump chamber 100 is formed by its two face sides 112 and 116, by a further and larger cylindrical jacket part 122, by the discharge opening 102, by the piston 17 expanded in the discharge region and by a gap 118. An armature part 106 connected to the piston 17, the armature part 106 being surrounded by a pot-shaped capsule 108, is situated inside the pump chamber 100. The jacket part 122 and the jacket part 11 can be composed of a single piece.

In the illustrated exemplary embodiment, the armature part 106 is fashioned pot-shaped, and is inverted over the core of an armature carrier 124 attached at the piston 17. The armature part 106 is fabricated of a magnetizable material, for example soft iron. In order to avoid interaction with the liquid medication, the capsule 108 is placed around the armature part 106 which is connected to the armature carrier 124 of the piston 17 such that a complete encapsulation of the armature part 106 is achieved.

A permanent magnet 110 is attached outside of the pump chamber 100. For example, the permanent magnet 110 may be a ring magnet which is placed at the outer housing 125 of the reciprocating pump 1 such that a force permanently acts on the armature part 106 which draws the latter away from the discharge opening 102. A face end 112 of the pump chamber 100 can serve as detent for this pull-off motion; preferably, however, the piston 17 has its end face 15 seated against the valve part 21 in order to avoid dead space in the admission chamber 7. When the armature carrier 124 is situated at the end piece 112, then the piston 17 is in a quiescent position. The permanent magnet 110 is preferably displaceable (not shown) in the direction of the longitudinal piston axis, whereby the re-storing force on the piston 17 is continuously adjustable. The ring magnet 110 is held between the cylindrical housing 125 and a magnetic return part 126.

The armature part 106 simultaneously serves as armature for an electro-magnetic drive system composed essentially of an electro-magnetic coil 114. This drive system is arranged at a defined location on the reciprocating pump 1. The only concern when selecting this location is that the magnetic field, generated when exciting the electromagnetic coil 114 with a current pulse, has an adequate force influence on the armature part 106 (which is then to be viewed as an armature for the coil 114), so that the piston 17 is conducted in the direction toward the discharge opening 102 until the capsule 108 contacts the other end face 116 of the pump chamber 100.

The functions of the permanent magnet 100 and of the armature part 106 can also be interchanged. An armature part of a permanent magnet material and a soft iron ring instead of the ring magnet would then be utilized. It is then not the permanent magnet 110, but rather the soft iron ring which is to be viewed as the outer component part of the magnetic spring system. It is also conceivable that the spring system is composed of a permanent magnet 110 situated outside of the pump chamber 100 and of an armature part 106 composed of a permanent magnetic material. Alternatively thereto, the permanent magnet 110 can also be arranged at the other side of the armature part 106, i.e. at that side facing toward the discharge opening 102; instead of an attractive force, a pressing force would then act on the armature part 106 to repel it away from the discharge opening 102.

When current flows in the coil 114, the piston 17 is thus moved in the direction of the discharge opening 102. It thereby presses the liquid medication, first, through the discharge line 104 and, then into the chamber which arises between the face wall 112 and the piston 17. It is pressed into the latter via the gap 118 which is fundamentally broader than the annular gap 31. When the flow of current through the coil 114 is interrupted, then the armature part 106 surrounded by the capsule 108 and surrounding the armature carrier 124 is conducted back to the first face side 112 by the permanent magnet 110, whereby the piston 17 connected to the armature carrier 124 is also conducted into its quiescent condition. During this return motion, the liquid medication which flowed from the reservoir 9 into the admission chamber 7 within the admission system 3 with the stroke of the piston 17 is conveyed through the gap 31 and 118 to the pump chamber 100.

The annular gap 31 thereby extends between a part of the jacket part 122 and the thinner part of the piston 17. This jacket part 122 forms the guide surface for the piston 17. When the piston 17 has returned into its quiescent position, then the pump chamber 100 is simultaneously refilled with liquid medication. The pump event repeats in the same way.

A dimension suitable for a medical application, for example, for an implantable insulin administering device, is a diameter of 2 mm for the piston 17 in the region of the gap 31. A single piston stroke of about 0.35 mm would then lead to a conveyed quantity of liquid of about 1 $\mu l$.

As a result of the spring system (partially lying outside of the fluid wing 3), formed by the permanent magnet 25 in the exemplary embodiment, an extremely small dead space in the admission chamber 7 itself results. The ratio of piston displacement to dead space is high, whereby a gas bubble existing in the admission line 5 is conveyed onward in an acceptable fashion. At the same time, no interactions between the spring system and the medication can occur. Thus there is no risk of a premature aging of the spring materials or of a toxification of the medication.

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. A reciprocating pump for moving a liquid comprising:
   means for reciprocably moving a piston in a jacket part, said piston having at least one planar end face;
   means for admitting liquid into an admission chamber, said planar end face of said piston forming one wall of said admission chamber;
   a valve part accommodated in said admission chamber in a freely moveable fashion for engaging said means for admitting liquid to periodically prevent liquid from entering said admission chamber and surrounded by said jacket part, the valve part being hollowed out such that at its sealing side it is inwardly arced with a cutting edge present at the edge which is presented resiliently against a valve seal in a quiescent condition of the reciprocating pump, said piston having its planar end face seated against a planar end face of the valve part in its quiescent position;
   a component part in magnetic interaction with said valve part and located external to said means for admitting liquid, said component part and said valve part forming a magnetic spring system for exerting a closing force on said valve part for engaging said means for admitting liquid, said component part being arranged outside of said means for admitting liquid;
   means for providing at least one gap between said jacket part and said valve part, and between said jacket part and said piston;
   a pump chamber having a discharge opening, said pump chamber being formed by two face sides, by a further and larger cylindrical jacket part, by said discharge opening, by said piston expanded in the discharge region and by said gap;

an armature part connected to said piston and surrounded by a pot-shaped capsule situated inside said pump chamber, said armature part being fabricated of a magnetizable material;

said capsule placed around said armature part, which is connected to an armature carrier of the piston, such that a complete encapsulation of the armature part is achieved;

a permanent magnet attached outside of the pump chamber as a ring magnet which is placed on an outer housing of said reciprocating pump such that a force permanently acts on said armature part which draws the latter away from said discharge opening, said armature part simultaneously serving as an armature for an electro-magnetic drive system composed essentially of an electro-magnetic coil;

said drive system being arranged at a defined location on the reciprocating pump such that when selecting his location when exciting the electro-magnetic coil with a current pulse, the magnetic field has an adequate force influence on said armature part so that said piston is conducted in the direction toward said discharge opening until said capsule contacts an end face of the pump chamber.

2. The reciprocating pump according to claim 1, wherein said permanent magnet is displaceable in the direction of a longitudinal piston axis.

* * * * *